(12) United States Patent
Barda et al.

(10) Patent No.: US 8,440,829 B2
(45) Date of Patent: May 14, 2013

(54) PI3 KINASE/MTOR DUAL INHIBITOR

(75) Inventors: David Anthony Barda, Indianapolis, IN (US); Mary Margaret Mader, Fishers, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 13/347,886

(22) Filed: Jan. 11, 2012

(65) Prior Publication Data

US 2012/0184577 A1  Jul. 19, 2012

Related U.S. Application Data

(60) Provisional application No. 61/432,958, filed on Jan. 14, 2011.

(51) Int. Cl.
*C07D 471/04* (2006.01)

(52) U.S. Cl.
USPC .......................................................... 546/82

(58) Field of Classification Search .................. None
See application file for complete search history.

(56) References Cited

FOREIGN PATENT DOCUMENTS

| WO | WO 03/097641 A2 | 11/2003 |
|---|---|---|
| WO | WO 2005/054237 A1 | 6/2005 |
| WO | WO 2006/122806 A2 | 11/2006 |
| WO | WO 2007/056112 A2 | 5/2007 |
| WO | WO 2007/106854 A2 | 9/2007 |
| WO | WO 2010/038165 A1 | 4/2010 |
| WO | WO 2010/139731 A1 | 12/2010 |
| WO | WO 2010/139747 A1 | 12/2010 |

OTHER PUBLICATIONS

Richard B. Silverman, The Organic Chemistry of Drug Design and Drug Action, Chapter 2: Drug Discovery, Design, and Development, Academic Press, p. 5-51 (1992).*

Polymorphism in Pharmaceutical Solids, Informa Healthcare, p. 318-335 (1999).*

Ivanisevic et al., Uses of X-Ray Powder Diffraction in the Pharmaceutical Industry, Pharma. Form. & Quality, 30-33 (Aug./Sep. 2011).*

* cited by examiner

*Primary Examiner* — Janet Andres
*Assistant Examiner* — Timothy R Rozof
(74) *Attorney, Agent, or Firm* — Danica Hostettler

(57) ABSTRACT

The present invention provides an imidazo[4,5-c]quinolin-2-one compound, or a pharmaceutically acceptable salt thereof, that inhibits both PI3K and mTOR and, therefore, is useful in the treatment of cancer.

6 Claims, No Drawings

PI3 KINASE/MTOR DUAL INHIBITOR

This application claims the priority of U.S. Provisional Application No. 61/432,958 filed 14 Jan. 2011.

The phosphoinositide 3-kinases (PI3Ks) are a family of lipid kinases that propagate intracellular signaling cascades regulating a wide range of cellular processes. For example, PI3K activation initiates a signal transduction cascade that promotes cancer cell growth, survival and metabolism. The mammalian target of rapamycin (mTOR) is a key signaling node coordinating cell cycle progression and cell growth in response to genetic, epigenetic, and environmental conditions. Pathways involved in mTOR signaling are dysregulated in precancerous human tissues. In view of the roles that PI3K and mTOR hold in cell cycle pathways, inhibition of both PI3K and mTOR may be useful in the treatment of certain human illnesses, such as cancer.

PI3K inhibitors and PI3K/mTOR dual inhibitors are known in the art. WO 2010/038165 discloses certain imidazo[1,5]naphthyridine compounds asserted to be modulators or inhibitors of the PI3-Kα enzyme and/or PI3-Kα/mTOR dual inhibitors. WO 2010/139731 and WO 2010/139747 disclose certain imidazoquinolinone compounds asserted for use in the treatment of protein or lipid kinase dependent diseases, particularly PI3K dependent diseases.

There remains a need to provide alternative PI3K/mTOR inhibitors, particularly potent PI3K/mTOR inhibitors with beneficial physical properties, such as improved solubility, and/or desirable clinical properties, such as improved in vivo potency and/or pharmacokinetic performance, which can be used in the treatment of cell proliferative disorders such as cancer. The present invention provides potent PI3K/mTOR inhibitors. More particularly, the present invention provides potent PI3K/mTOR inhibitors with beneficial physical properties and/or desirable clinical properties that are useful as anticancer agents.

The present invention provides a compound which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof.

As a particular embodiment, the present invention provides the compound which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one.

Another embodiment is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one in crystalline form.

The present invention also provides 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one in crystalline form characterized by a X-ray powder diffraction pattern having characteristic peaks, in 2θ±0.2, occurring at 8.57 and one or more of 9.06, 15.93, 18.29, and 18.87.

The present invention provides a pharmaceutical composition comprising 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof, and a pharmaceutically acceptable carrier, diluent, or excipient.

The present invention provides a pharmaceutical composition comprising 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof, additionally comprising one or more therapeutic ingredients.

The present invention provides a method of treating cancer, comprising administering to a patient in need thereof an effective amount of 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof.

The present invention provides the use of 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof, for the manufacture of a medicament for the treatment of cancer.

The present invention provides 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof, for use in therapy.

The present invention provides 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof, for use in the treatment of cancer.

Furthermore, the present invention provides preferred embodiments of the methods and uses as described herein, in which cancer is selected from the group consisting of bladder cancer, colon cancer, gastric cancer, head and neck cancer, NSCLC, breast cancer, melanoma, ovarian cancer, pancreatic cancer, prostate cancer, glioblastoma, lung cancer, renal cancer, sarcoma, hematopoietic and lymphoid tissue cancer, CNS cancer, cervical cancer, endometrial cancer, liver cancer, skin cancer, stomach cancer, thyroid cancer, upper aerodigestive tract cancer, and urinary cancer.

As used above, and throughout the description of the invention, the following terms, unless otherwise indicated, shall be understood to have the following meanings:

"Pharmaceutically acceptable salt" or "pharmaceutically acceptable salts" refers to the relatively non-toxic, inorganic and organic salts of compounds of the present invention.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

"Therapeutically effective amount" or "effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal, or human that is being sought by the researcher, veterinarian, medical doctor, or other clinician.

The compounds of the present invention are capable of reaction, for example, with a number of inorganic and organic acids to form pharmaceutically acceptable salts. Such pharmaceutically acceptable salts and common methodology for preparing them are well known in the art. See, e.g., P. Stahl, et al., Handbook of Pharmaceutical Salts: Properties, Selection, and Use, (VCHA/Wiley-VCH, 2002); S. M. Berge, et al., "Pharmaceutical Salts", *Journal of Pharmaceutical Sciences*, Vol. 66, No. 1, January 1977.

The compounds of the present invention are preferably formulated as pharmaceutical compositions using one or more pharmaceutically acceptable carriers, diluents, or excipients and administered by a variety of routes. Preferably, such compositions are for oral, subcutaneous, or intravenous administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The amount of compound of the present invention actually administered will be determined by a physician under the relevant circumstances, including the condition to be treated, the chosen route of administration, the actual compound of the present invention administered, the age, weight, and response of the individual patient, and the severity of the patient's symptoms. Dosages per day normally fall within the range of about 1 mg to about 2000 mg. In some instances dosage levels below the lower limit of the aforesaid range may be more than adequate, while in other cases still larger doses may be employed.

The compounds of the present invention may be prepared by a variety of procedures known in the art, as well as those described in the Preparations and Examples below. The specific synthetic steps for each of the routes described may be combined in different ways to prepare the compounds of the present invention.

The reagents and starting materials are generally readily available to one of ordinary skill in the art. Others may be made by standard techniques of organic and heterocyclic chemistry, techniques which are analogous to the syntheses of known structurally similar compounds and the procedures described in the Preparations and Examples which follow, including any novel procedures. The following Preparations and Examples are provided to illustrate the invention in further detail and represent typical syntheses of the compounds. The names of the compounds of the present invention are generally provided by SymyxDraw 3.2.

As used herein, the following terms have the meanings indicated: As used herein, the following terms have the meanings indicated: "ATP" refers to adenosine triphosphate; "AUC" refers to area under the curve; "CNS" refers to central nervous system; "DMEM" refers to Dulbecco's modified eagle medium; "DMSO" refers to dimethylsulfoxide; "DTT" refers to dithiothreitol; "4E-BP1" refers to 4E binding protein 1; "FBS" refers to fetal bovine serum; "EDTA" refers to ethylenediaminetetraacetic acid; "EGTA" refers to ethylene glycol-bis(α-amino ethylether)-N,N,N',N'-tetraacetic acid; "GFP" refers to green fluorescent protein; "GST" refers to glutathione-S-transferase; "HEC" refers to hydroxyethylcellulose; "HEPES" refers to N-2-hydroxyethylpiperazine-N'-2-ethanesulfonic acid; "HPLC" refers to high-pressure liquid chromatography; "IC50" refers to half maximal inhibitory concentration; "IMDM" refers to Iscove's Modified Dulbecco's Media; "MEM" refers to minimum essential medium; "MS" refers to mass spectroscopy; "NMR" refers to nuclear magnetic resonance; "NSCLC" refers to non-small cell lung cancer; "PBS" refers to phosphate-buffered saline; "PGK" refers to phosphoglycerate kinase; "PIP2" refers to phosphatidylinositol (4,5) bisphosphate; "PO" refers to per oral; "POPS" refers to palmitoyl-oleoyl phosphatidylserine; "PPI" refers to proton pump inhibitor; "RPMI" refers to Roswell Park Memorial Institue; "RT" refers to room temperature; "TFA" refers to trifluoroacetic acid; "TMED50" refers to threshold minimum effective dose; "TR-FRET" refers to time resolved fluorescent energy transfer; "Tris" refers to tris(hydroxymethyl)aminomethane; "Triton-X" refers to 4-(1,1,3,3-tetramethylbutyl)phenyl-polyethylene glycol t-octylphenoxypolyethoxyethanol polyethylene glycol tert-octylphenyl ether; and "Tween-20" refers to polysorbate 20; "XRD" refers to X-Ray powder diffraction.

Preparation 1

(2S)-2-Methoxypropan-1-amine hydrochloride

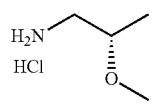

Cool a solution of tert-butyl[(2S)-2-hydroxypropyl]carbamate (870 g, 4.96 mol) in tetrahydrofuran (10 L) to 5° C. Add sodium hydride (60% dispersion, 248 g, 6.21 mol, 1.25 eq.) in portions over 8 minutes. Stir the reaction at 5° C. for 30 minutes. Add methyl iodide (387 mL, 6.21 mol, 1.25 eq.) dropwise over 5 minutes and allow the reaction to proceed at 5-10° C. for 45 minutes. Quench the reaction with water (1 L) and extract with ethyl acetate (4 L). Obtain the organic layer and concentrate it in vacuo to obtain a residue. Co-evaporate the residue with toluene (2×1 L), dilute with dichloromethane (2 L) and filter. Rinse remaining solid with additional dichloromethane (500 mL). Concentrate the combined dichloromethane liquid filtrate in vacuo to obtain a crude intermediate of tert-butyl N-[(2S)-2-methoxypropyl]carbamate (880 g, 94%).

Suspend the crude intermediate tert-butyl N-[(2S)-2-methoxypropyl]carbamate (806 g, 4.26 mmol) in dichloromethane (3.22 L) and add 4M HCl in dioxane (2.66 L) dropwise at 15° C. over 30 minutes. Stir the mixture at room temperature for 2 hours. Filter and wash solid residue with additional dichloromethane (2×250 mL) and remove volatiles in vacuo to give a solid precipitate. Add methyl tert-butyl ether (2 L) to the solid and filter; wash the solid with additional methyl tert-butyl ether (2×500 mL), dry and further wash the solid with acetone (4×500 mL) to obtain a white solid as the titled compound (171 g, 32%). 1H NMR (300.13 MHz, DMSO): 8.11 (s, 3H), 3.62-3.55 (m, 1H), 3.26 (s, 3H), 2.87 (dd, J=3.6, 13.2 Hz, 1H), 2.68 (dd, J=8.5, 13.2 Hz, 1H), 1.10 (d, J=6.3 Hz, 3H).

Preparation 2

Ethyl 6-bromo-4-chloro-quinoline-3-carboxylate

Suspend 6-bromo-4-hydroxyquinoline-3-carboxylic acid ethyl ester (11 g, 37 mmol) in anhydrous dimethylformamide (148.6 mL) under nitrogen atmosphere. Add phosphoryl chloride (20.7 mL, 222 mmol, 6 eq.) via syringe over 5 minutes and stir vigorously at room temperature for 3 hours. Quench the reaction by pouring the mixture into ice water (1.5 L) and continue stirring until all the ice has melted. Obtain the solid formed by filtration, rinse with water and allow complete drying to afford the titled compound (11.4 g, 94%). MS (ESI) m/z (M+H)$^+$314.0, 316.0.

Alternately, prepare 6-bromo-4-hydroxyquinoline-3-carboxylic acid ethyl ester as follows and use in preparation of titled compound. Dissolve diethyl 2-(((4-bromophenyl)amino)methylene)malonate (25.6 g, 74.8 mmol) in 2-methyltetrahydrofuran (107 mL) and transfer to a pump. The pump then feeds between 19 and 21 mL of this solution to a 25 mL reactor between 240° C. and 260° C. under between 575 to 700 psi nitrogen to remain above the vapor pressure of the reagent solution. After between 60 and 180 minutes at this temperature, the resulting slurry exits the reactor through a valve via a diptube to near the bottom of the reactor to a 10 mL depressurization and cooling zone. Finally, a second valve in series sends the slurry to an in-line pressure filter. This sequence to empty the reactor is repeated 2 additional times before refilling the reactor as described above to ensure the residual slurry is removed to a minimal volume and to provide nitrogen pressure to the single plate filter. The automated cycle continues repeatedly and solids build up on the same single plate filter over time. If production run is done for several days, at least 2 filters in parallel would be used, so that the off-line filter could be washed and solids removed without stopping the intermittent flow reactor. After an additional 5 cycles are performed in this fashion 2-methyltetrahydrofuran (20 mL) is sent to the reactor and transferred to the filter. This operating mode can be called intermittent flow semi-continuous or sequenced automated batch. Either way, the aspects of this operating mode that make it similar to continuous reaction are that the reactor temperature and pressure do not change with time but always remain at reaction conditions, heat up and cool down times are very fast for reagents flowing into the reactor and product flowing out of reactor, heat-up plus cool down times are scalable, and residence time of reagents and products in the reaction vessel are the same at all scales by controlling flows in and out and the ability to heat/cool external to the reactor. After drying, the 6-bromo-4-hydroxyquinoline-3-carboxylic acid ethyl ester is collected (4.66 g, 21%). The resulting diethyl 2-(((4-bromophenyl)amino)methylene)malonate rich filtrates are concentrated to remove ethanol yielding 7.8 g and reconstituted in 2-methyltetrahydrofuran. A portion of this material (4.8 g) is resubjected to the reaction conditions and additional 6-bromo-4-hydroxyquinoline-3-carboxylic acid ethyl ester (0.56 g) is collected for an overall yield of 25%. $^1$H-NMR: (399.84 MHz, TFA-d), δ (ppm): 1.52 (3H, t, J=7.04 Hz), 4.67 (2H, q, J=7.03 Hz), 8.03 (1H, d, J=8.79 Hz), 8.28 (1H, d, J=8.79 Hz), 8.80 (1H, s), 9.32 (1H, s); $^{13}$C NMR (100.54 MHz, TFA-d), δ (ppm): 11.9, 64.7, 105.3, 121.0, 121.2, 124.9, 126.9, 137.9, 141.1, 145.0, 167.2, 172.4.

Preparation 3

2-(5-Bromo-3-pyridyl)propan-2-ol

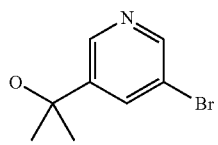

Method 1

Add a solution of ethyl 5-bromopyridine-3-carboxylate (22.5 g, 98 mmol) in tetrahydrofuran (350 m L) to a solution of 3M methylmagnesium bromide in diethyl ether (98 mL, 293 mmol, 3 eq.) with internal temperature below 30'C. Upon completion of reaction, cool the mixture in an ice bath and quench with saturated aqueous ammonium chloride and keep stirring until most solids dissolve. Add water (500 mL) and extract with ethyl acetate (3×500 mL). Dry the organic layer over sodium sulfate, filter and concentrate the organic layer to a residue. Purify the residue by silica gel column chromatography eluting with solvent of ethyl acetate:hexane (1:1), to afford the titled product as an oil (19.4 g, 92%). MS (ESI) m/z (M+H)$^+$214.9, 216.9.

Method 2

Add a solution of methyl 5-bromopyridine-3-carboxylate (173 g, 800 mmol) in tetrahydrofuran (2.6 L) dropwise to a 3 M solution of methylmagnesium bromide in diethyl ether (800 mL, 3.0 eq.) over 30 minutes in a cooling bath with internal temperature below 18° C. Stir the mixture at room temperature for one hour, then cool it to 0° C. and quench with saturated aqueous ammonium chloride (500 mL). Add saturated aqueous sodium bicarbonate solution (1 L) and allow separation of layers. Obtain the organic layer and concentrate it with toluene (1 L) to azeotrope residual water to afford the title compound (168 g, 97%) as orange oil. 1H NMR (300.13 MHz, DMSO): 8.66 (d, J=1.9 Hz, 1H), 8.55 (d, J=2.2 Hz, 1H), 8.06 (t, J=2.2 Hz, 1H), 5.38 (s, 1H), 1.45 (s, 6H).

Preparation 4

2-[5-(4,4,5,5-tetramethyl-1,3,2-dioxaborolan-2-yl)-3-pyridyl]propan-2-ol

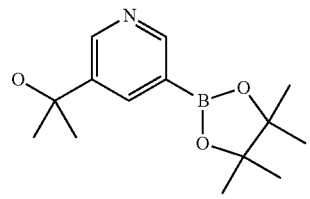 [SMILES: CC(C)(O)c1cncc(B2OC(C)(C)C(C)(C)O2)c1]

Purge with a mixture of 2-(5-bromo-3-pyridyl)propan-2-ol (18.5 g, 85.7 mmol), bis(pinacolato)diboron (44 g, 171 mmol, 2 eq.) and potassium acetate (25.2 g, 257 mmol, 3 eq.) in 1,4-dioxane (428 mL) in nitrogen thoroughly. Add (1,1'-bis(diphenylphosphino)ferrocene)palladium(II) chloride (3.5 g, 4.3 mmol) and evacuate and purge the reaction twice with nitrogen. Heat the mixture at 90° C. overnight. Cool and dilute with ethyl acetate (1 L) and sonicate for 30 minutes. Filter through a pad of Celite® and dry the liquid filtrate over sodium sulfate. After filtration, concentrate the organic liquid and re-dissolve residue in ethyl acetate (1 L) and filter again through a pad of Celite®. Concentrate the filtrate and suspend the residue in diethyl ether (100 mL) followed by hexane (700 mL). Sonicate briefly and filter to obtain solid residue to afford the titled compound as a crude solid (18.5 g). MS (ESI) m/z (M+H)$^+$264.0.

Preparation 5

Ethyl 6-bromo-4-[[(2S)-2-methoxypropyl]amino]quinoline-3-carboxylate

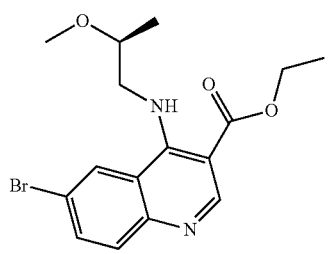 [SMILES: CCOC(=O)c1cnc2ccc(Br)cc2c1NC[C@H](C)OC]

Suspend ethyl-6-bromo-4-chloro-quinoline-3-carboxylate (389 g, 1.24 mol) and (2S)-2-methoxypropan-1-amine, hydrochloride (171 g, 1.36 mol, 1.1 eq.) in ethanol (5.84 L). Add diisopropylethylamine (474 mL) and heat the mixture at 50° C. overnight. After 16 hours, cool the reaction to room temperature and concentrate in vacuo. Add methyl tert-butyl ether (2 L) to the residue and stir for 20 min. Filter the precipitate and wash it with methyl tert-butyl ether (2×250 mL). Concentrate the filtrate in vacuo to afford the titled compound in almost quantitative yield. The compound will be used in the next step without further purification. MS (ESI) m/z (M+H)$^+$367.0, 369.0.

Preparation 6

6-Bromo-4-[[(2S)-2-methoxypropyl]amino]quinoline-3-carboxylic acid

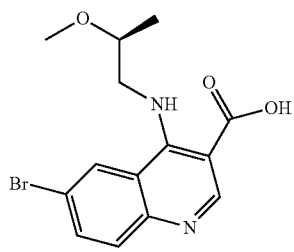 [SMILES: CO[C@@H](C)CNc1c(C(=O)O)cnc2ccc(Br)cc12]

Add a solution of sodium hydroxide (296.7 g, 7.42 mol, 6 eq.) in water (454 mL) to a solution of ethyl 6-bromo-4-[[(2S)-2-methoxypropyl]amino]quinoline-3-carboxylate (454 g, 1.24 mol) in tetrahydrofuran (4.54 L) at room temperature. Heat the mixture at 50° C. overnight. After 18 hours, cool the reaction to 0° C., add 37% aq. HCl dropwise over 30 minutes until pH=6 (ca. 450 mL) with the temperature under 23° C. Filter the precipitate formed with filter paper and wash it with water (2 L), acetone (2 L) and methyl tert-butyl ether (2 L) subsequently. Dry the white solid to give the titled compound (359 g, 86%). MS (ESI) m/z (M+H)$^+$338.9, 340.9.

Preparation 7

8-Bromo-1-[(2S)-2-methoxypropyl]-3H-imidazo[4,5-c]quinolin-2-one

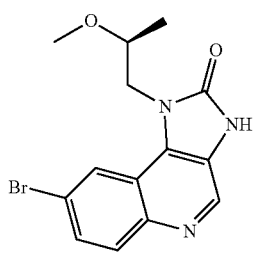 [SMILES: CO[C@@H](C)Cn1c(=O)[nH]c2cnc3ccc(Br)cc3c21]

Suspend 6-bromo-4-[[(2S)-2-methoxypropyl]amino]quinoline-3-carboxylic acid (510 g, 1.5 mol) in dimethylformamide (7.65 L) and add triethylamine (419 mL, 3 mol, 2 eq.) at 70° C. Add diphenylphosphonic azide (390 mL, 1.8 mol., 1.2 eq.) dropwise over 30 minutes. Heat the mixture to 70° C. (internal temperature) for 1 hour. Cool to 10° C. and dilute with water (5 L). Stir the mixture for 1 hour, filter the precipitate, wash it with water (2×1 L) and methyl tert-butyl ether (2×1 L), and then let it dry to give the titled compound as a white solid (445 g, 88%). MS (ESI) m/z (M+H)$^+$335.9, 337.9.

Preparation 8

8-Bromo-1-[(2S)-2-methoxypropyl]-3-methyl-imidazo[4,5-c]quinolin-2-one

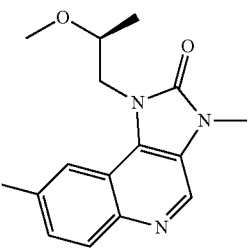

Method 1

Suspend 8-bromo-1-[(2S)-2-methoxypropyl]-3H-imidazo[4,5-c]quinolin-2-one (10 g, 30 mmol) and tetra-N-butylammonium bromide (3 g, 9.3 mmol) in dichloromethane (150 mL). Add 2M aqueous sodium hydroxide (75 mL, 150 mmol) at room temperature. Add iodomethane (7.5 mL, 120 mmol) and stir the mixture vigorously overnight at 28° C. Allow phase separation to occur. Concentrate the organics in vacuo. Wash the residue with acetone (50 mL) to remove tetra-N-butylammonium bromide. Filter the mixture to give the titled compound as solid powder (5 g, 48%). MS (ESI) m/z (M+H)$^+$ 350.0, 352.0.

Method 2

Suspend 8-bromo-1-[(2S)-2-methoxypropyl]-3H-imidazo[4,5-c]quinolin-2-one (285 g, 847.7 mmol) and tetra-N-butylammonium bromide (82 g, 254 mmol) in dichloromethane (2.85 L). Add 2 M aqueous sodium hydroxide (1.7 L, 3.4 mol) at room temperature. Add dimethyl sulfate (160.8 mL, 1.7 mol) and stir the mixture vigorously for 3 hours. Allow phase separation and obtain the organic layer. Concentrate the organic layer in vacuo and slurry with water (2.4 L) for 30 minutes. Filter the solid precipitate formed and wash it with water (2×500 mL), hexane (2×500 mL) and dry. The titled compound is obtained as a white solid (207 g, 70%). MS (ESI) m/z (M+H)$^+$ 350.0, 352.0.

Method 3

Suspend 8-bromo-1-[(2S)-2-methoxypropyl]-3H-imidazo[4,5-c]quinolin-2-one (50 g, 149 mmol) and tetra-N-butylammonium bromide (14.4 g, 44.7 mmol) in dichloromethane (500 mL). Add 8% sodium hydroxide solution (600 mmol). Add iodomethane (23.2 g, 163.4 mmol) and stir at room temperature for 22 hrs. Organic phase is separated and washed with water (250 mL). Then the organic phase is concentrated and recrystallized from dichloromethane, then is dried below 65° C. to give title compound (42.7 g, 82%). 1H NMR (CDCl$_3$, 400 MHz) δ 8.70 (s, 1H), 8.50 (d, 1H, J=2.4 Hz), 7.97 (d, 1H, J=9.2 Hz), 7.65 (d, 1H, J=9.2, 2 Hz), 4.32 (m, 2H), 3.82 (m, 1 H), 3.79 (s, 3H), 3.28 (s, 3H), 1.32 (d, 3H, J=6.4 Hz).

Preparation 9

Ethyl 5-(4,4,5,5-tetramethyl-1,3,2-dioxaborolan-2-yl)pyridine-3-carboxylate

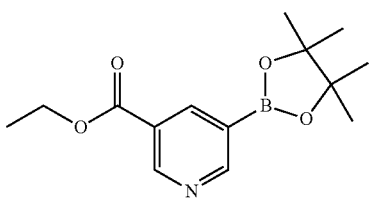 [SMILES: CCOC(=O)c1cncc(B2OC(C)(C)C(C)(C)O2)c1]

Add tris(dibenzylideneacetone)dipalladium(0) (3.98 g, 4.35 mmol), tricyclohexylphosphine (2.44 g, 8.7 mmol) and potassium acetate (42.65 g, 435 mmol) to a solution of bis(pinacolato) diboron (35.88 g, 141.3 mmol) in dimethylformamide (175 mL). Bubbling $N_2$ into the mixture for 15 minutes, then heat it to 80~85° C. Then add ethyl 5-bromonicotinate (25.0 g, 108.8 mmol) in dimethylformamide (75 mL) slowly to the mixture at 80~85° C., and stir the formed mixture at 80~85° C. for 4-5 hours. Cool the reaction mixture to 15-35° C., and then add methyl tertiary butyl ether (250 mL) and water (250 mL). Filter the mixture with diatomite and separate the organic and aqueous layers. Back extract the aqueous layer with methyl tertiary butyl ether (250 mL). Wash the combined organic layer with brine (150 mL) and water (150 mL). Concentrate the organic under vacuum, re-crystallize the crude product with methyl tertiary butyl ether/heptane (1:6), and then dry it below 55° C. to give the title compound as a grey solid (18.67 g, 62%). $^1$H NMR (acetone-$d_6$, 400 MHz) δ40-1.43 (m, 15H), 4.44 (q, J=7.1 Hz, 2H), 8.57 (t, J=1.9 Hz, 1H), 9.02 (d, J=1.5 Hz, 1H), 9.225 (d, J=2.3 Hz, 1H).

Preparation 10

Ethyl 5-[1-[(2S)-2-methoxypropyl]-3-methyl-2-oxo-imidazo[4,5-c]quinolin-8-yl]pyridine-3-carboxylate

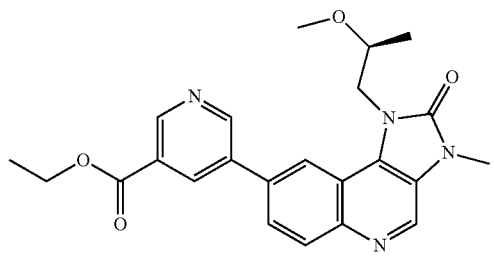 [SMILES: CCOC(=O)c1cncc(-c2ccc3ncc4c(c3c2)n(C[C@H](C)OC)c(=O)n4C)c1]

To a three-necked flask containing 8-bromo-1-[(2S)-2-methoxypropyl]-3-methyl-imidazo[4,5-c]quinolin-2-one (35 g, 100 mmol), ethyl 5-(4,4,5,5-tetramethyl-1,3,2-dioxaborolan-2-yl)pyridine-3-carboxylate (29.1 g, 105 mmol), sodium ethyl acetate (28.7 g, 350 mmol), 1,1'-bis(diphenylphosphino)ferrocene-palladium(II)dichloride dichloromethane (0.817 g, 1.0 mmol) add 1,4-dioxane (200 mL) and water (200 mL) under $N_2$. Then heat the reaction mixture to 85° C. and continue stirring for 10 hours. Cool the reaction mixture to room temperature. Filter the mixture with Kieselguhr® Silica-Thiol to remove the catalyst. Add water (400 mL) drop wise and solid precipitates. Filter the mixture and wash the solid with water (400 mL). Stir the solid in ethyl acetate (70 mL) at room temperature for one hour; filter, wash with ethyl acetate (70 mL), and dry under vacuum below 65° C. to give the title compound (33.6 g, 80%). $^1$H NMR (CDCl$_3$, 400 MHz) δ 9.25 (d, 1H, J=2 Hz), 9.15 (d, 1H, J=2.4 Hz), 8.75 (s, 1H), 8.73 (d, 1H, J=1.6 Hz), 8.65 (t, 1H), 8.24 (d, 1H, J=8.8 Hz), 7.89 (dt, 1H, J=8.8, 1.6 Hz), 4.47 (q, 2H), 4.38 (m, 2H), 3.90 (m, 1H), 3.64 (s, 3H), 3.26 (s, 3H), 1.45 (t, 3H), 1.37 (d, 3H, J=6 Hz).

EXAMPLE 1

8-[5-(1-Hydroxy-1-methylethyl)pyridin-3-yl]-1-[(2S)-2-methoxypropyl]-3-methyl-1,3-dihydro-2H-imidazo[4,5-c]quinolin-2-one

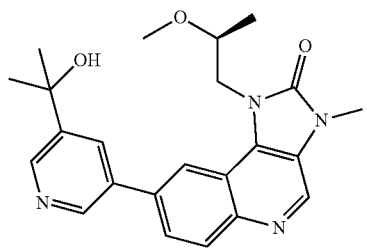 [SMILES: CO[C@@H](C)Cn1c(=O)n(C)c2cnc3ccc(-c4cncc(C(C)(C)O)c4)cc3c21]

Method 1

Dissolve 8-bromo-1-[(2S)-2-methoxypropyl]-3-methyl-imidazo[4,5-c]quinolin-2-one (0.600 g, 1.7 mmol) and 2-[5-(4,4,5,5-tetramethyl-1,3,2-dioxaborolan-2-yl)-3-pyridyl]propan-2-ol (0.9 g, 3.43 mmole) in tetrahydrofuran (75 mL) and water (7.5 mL) in a sealed tube. Purge the mixture with nitrogen. Add potassium fluoride (400 mg, 6.89 mmole), tris(dibenzylideneacetone)dipalladium (0) (200 mg, 0.22 mmole) and tri-tert-butylphosphonium tetrafluoroborate (200 mg, 0.68 mmole). Seal the reaction in nitrogen and heat at 65-70° C. overnight. Cool the mixture to room temperature, filter to remove inorganic residue. Concentrate the filtrate and dilute it with dichloromethane (120 mL) and water (30 mL). Separate the organic layer and dry it over magnesium sulfate powder. Concentrate it in vacuo to brown oil. Purify the residue by silica gel column chromatography with eluting solvent of 30-65% ethyl acetate in hexane, then with 0-7% methanol in dichloromethane. Concentrate fractions containing the product and co-evaporate with diethyl ether (2×10 mL), acetone (10 mL), acetone and diethyl ether (10 mL each) subsequently. Dry the solid residue to afford the titled compound as an orange powder (0.30 g, 44%). MS (ESI) m/z (M+H)$^+$407.0.

Method 2

Purge nitrogen through a suspension of 2-(5-bromo-3-pyridyl)propan-2-ol (100 g, 464 mmol, 1.25 eq.), 4,4,5,5-tetramethyl-2-(4,4,5,5-tetramethyl-1,3,2-dioxaborolan-2-yl)-1,3,2-dioxaborolane (141.4 g, 557 mmol, 1.5 eq.), and potassium acetate (127.5 g, 1.3 mol) in 1,4-dioxane (2.6 L) for 30 minutes at room temperature. Add dichloro-((bis-diphenylphosphino)ferrocenyl)-palladium(II) dichloromethane adduct (9 g, 11.14 mmol) under nitrogen and heat the mixture to 90° C. Stir the mixture for 3 hours. Cool the reaction mixture to 80° C. and then add 8-bromo-1-[(2S)-2-methoxypropyl]-3-methyl-imidazo[4,5-c]quinolin-2-one (130 g, 371 mmol), a solution of sodium carbonate (118 g, 1.1 mol) in water (910 mL), and dichloro-((bis-diphenylphosphino)ferrocenyl)-palladium(II) dichloromethane adduct (9 g, 11.14 mmol). Stir the mixture for 1.5 hours at the same temperature. Allow phase separation to obtain the organic layer and cool it to 40° C. before concentration in vacuo. Purify the residue (350 g) by silica gel column chromatography with an eluting solvent mixture gradient of dichloromethan/ethyl acetate/methanol from 1:1:1 to 1:1:20. Obtain product-containing fractions. Concentrate and slurry the residue in ethyl acetate (10 L/kg) at 40° C. for 15 minutes, filter and wash the solid with ethyl acetate (2×1 L/kg) and methyl tert-butyl ether (2×2 L/kg). Dissolve the washed solid in methanol (10 L/kg), treat with SiliaBond® Thiol (0.4 g/g) to remove residual metal. Stir the suspension at 23° C. for 4 h, and filter. Wash the solid with methanol (1 L/kg). Combine all filtrate and methanol washes and concentrate in vacuo. Retain the solid in solvent (about 100 mL). Material crystallizes from the solvent. Filter solid material and dry at 1 mbar/40° C. overnight to afford the titled compound as a white solid (77 g, 51%). MS (ESI) m/z (M+H)+407.1. 1H NMR (500.23 MHz, DMSO): 9.05 (s, 1H), 8.95 (d, J=2.2 Hz, 1H), 8.79 (d, J=2.0 Hz, 1H), 8.69 (d, J=1.5 Hz, 1H), 8.33 (t, J=2.1 Hz, 1H), 8.18 (d, J=8.8 Hz, 1H), 8.12 (dd, J=1.7, 8.8 Hz, 1H), 5.41 (s, 1H), 4.56 (dd, J=8.3, 15.2 Hz, 1H), 4.37 (dd, J=4.2, 15.2 Hz, 1H), 3.85-3.80 (m, 1H), 3.57 (s, 3H), 3.12 (s, 3H), 1.56 (d, J=1.2 Hz, 6H), 1.26 (d, J=6.1 Hz, 3H).

Method 3

To a solution of ethyl 5-[1-[(2S)-2-methoxypropyl]-3-methyl-2-oxo-imidazo[4,5-c]quinolin-8-yl]pyridine-3-carboxylate (32.0 g, 76.1 mmol) in tetrahydrofuran (320 mL), slowly add MeMgBr (1.4M in tetrahydrofuran/toluene, 221.4 g, 6.92×) solution under $N_2$ protection with temperature below 0° C. Stir the mixture at −5~0° C. for one hour under $N_2$ protection. Add $NH_4Cl$ solution (15%, 320 mL) slowly to quench the reaction while keeping the temperature below 25° C. Then add ethyl acetate (320 mL). Warm up the mixture to 25~30° C. and stir for half hour. After separation of two layers, back extract the aqueous layer with tetrahydrofuran (160 mL). Wash the combined organic with brine (192 mL). Add active charcoal (1.6 g) to the organic layer and stir at 65~75° C. for 4-5 hours. Filter the mixture with Kieselguhr® Silica-Thiol (1.6 g). Stir the organic layer at 65~75° C. for 2-3 hours; the mixture is then filtered by Kieselguhr® Silica-Thiol. The organic layer is removed under vacuum and the re-crystallized with ethyl acetate/tetrahydrofuran to give 8-[5-(1-hydroxy-1-methylethyl)pyridin-3-yl]-1-[(2S)-2-methoxypropyl]-3-methyl-1,3-dihydro-2H-imidazo[4,5-c] quinolin-2-one as a light yellow solid (22.34 g, 72.2%).

To a three-necked flask add 8-[5-(1-hydroxy-1-methylethyl)pyridin-3-yl]-1-[(2S)-2-methoxypropyl]-3-methyl-1, 3-dihydro-2H-imidazo[4,5-c]quinolin-2-one prepared as above in this Method 3 (50.0 g, 123 mmol) and tetrahydrofuran (1500 mL). Stir the mixture and heat it to 45-55° C. to form an absolute solution. Filter and concentrate the filtrate under vacuum below 45° C. to 2.0-3.0V and add ethyl acetate (500 mL), then concentrate under vacuum below 45° C. to 7~8V. Stir the slurry at 70~80° C. for 6-10 hours, then cool to 20~25° C. and filter. Add ethyl acetate (135-140 g) and ethanol (13.5-14.0 g) to the residue. Stir the slurry at 70~80° C. for 6-10 hours; then cool to 20~25° C. and filter. Concentrate under vacuum to give the title compound as pale yellow solid (37.9 g, 75.8%). $^1$H NMR (CDCl$_3$, 400 MHz) δ 8.86 (d, 1H, J=2 Hz), 8.76 (d, 1H, J=2.4 Hz), 8.71 (s, 1H), 8.64 (d, 1H, J=1.6 Hz), 8.21 (t, 2H), 7.85 (d, 1H, J=6.8 Hz), 4.36 (q, 2H), 3.88 (m, 1H), 3.62 (s, 3H), 3.23 (s, 3H), 2.79 (s, 1H), 1.95 (s, 1H), 1.71 (d, 6H, J=0.8 Hz), 1.33 (d, 3H, J=6.4 Hz).

EXAMPLE 2

8-[5-(1-Hydroxy-1-methylethyl)pyridin-3-yl]-1-[(2S)-2-methoxypropyl]-3-methyl-1,3-dihydro-2H-imidazo[4,5-c]quinolin-2-one, Form I Method 1

The impure free base (Example 1) is slurried in ethylacetate, with a white solid starting to precipitate from a brownish solution. The solid is filtered in a glove box placed inside the ventilation hood and is allowed to dry in the vacuum inside the glove box overnight. The product is left under vacuum overnight (11 g, 63.18% yield).

The X-Ray powder diffraction (XRD) patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

Thus, a prepared sample of the compound is characterized by an XRD pattern using CuKa radiation as having diffraction peaks (2-theta values) as described in Table 1 below. Specifically the pattern contains characteristic peaks occurring at 8.57 and one or more of 9.06, 15.93, 18.29 and 18.87 with a tolerance for the diffraction angles of 0.2 degrees.

TABLE 1

X-ray powder diffraction peaks of Example 2, Method 1

| Peak | Angle (2-Theta °) | Intensity (%) |
|---|---|---|
| 1 | 8.57 | 100.00 |
| 2 | 9.06 | 35.40 |
| 3 | 9.44 | 13.30 |
| 4 | 10.22 | 10.60 |
| 5 | 11.90 | 13.10 |
| 6 | 13.57 | 20.10 |
| 7 | 14.07 | 15.60 |
| 8 | 15.93 | 32.50 |
| 9 | 18.29 | 73.40 |
| 10 | 18.87 | 74.50 |
| 11 | 20.40 | 16.70 |
| 12 | 21.57 | 16.10 |
| 13 | 23.19 | 30.70 |
| 14 | 25.54 | 21.90 |
| 15 | 27.47 | 19.80 |
| 16 | 32.17 | 9.60 |

Method 2

Dissolve a reasonable amount of the free base of Example 1 in ethanol or tetrahydrofuran to make a solution. Evaporate the solution to provide the title compound.

Thus, a prepared sample of the title compound is characterized by an XRD pattern using CuKa radiation as having diffraction peaks (2-theta values) as described in Table 1 below. Specifically the pattern contains characteristic peaks occurring at 8.60 in combination with one or more of the peaks selected from the group consisting of 9.08, 15.93, 18.25 and 18.83 with a tolerance for the diffraction angles of 0.2 degrees.

TABLE 2

X-ray powder diffraction peaks of Example 2, Method 2

| Peak | Angle (2-Theta °) | Intensity (%) |
|---|---|---|
| 1 | 8.60 | 70.1 |
| 2 | 9.08 | 36.5 |
| 3 | 9.46 | 15.3 |
| 4 | 10.23 | 17.9 |
| 5 | 11.91 | 17.2 |
| 6 | 13.15 | 11.5 |
| 7 | 13.57 | 13.7 |
| 8 | 14.08 | 23.0 |
| 9 | 15.93 | 47.1 |
| 10 | 18.25 | 80.4 |
| 11 | 18.83 | 100.0 |
| 12 | 20.61 | 22.9 |
| 13 | 21.54 | 22.3 |
| 14 | 23.16 | 13.1 |
| 15 | 25.52 | 39.6 |
| 16 | 26.13 | 39.6 |
| 17 | 27.43 | 16.9 |
| 18 | 28.55 | 14.2 |
| 19 | 29.48 | 17.4 |
| 20 | 32.13 | 12.1 |

EXAMPLE 3

8-[5-(1-Hydroxy-1-methylethyl)pyridin-3-yl]-1-[(2S)-2-methoxypropyl]-3-methyl-1,3-dihydro-2H-imidazo[4,5-c]quinolin-2-one monohydrate

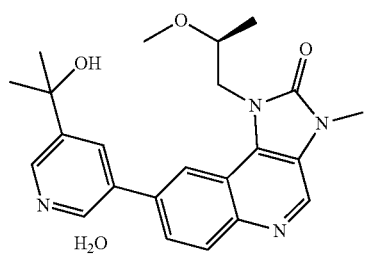

Example 3 can be prepared by slurrying a mixture of a methanolate form of the free base (methanolate is a crystal form obtained from a methanol solution of free base), along with anhydrous form of the free base (see Example 2) in reasonable amount of water for 24 hours. Alternatively, suspend the anhydrous form of the free base (see Example 2) in a solution of acetone/water (ratio 95:5, $a_w$=0.57) and seeding with the monohydrate form will result in a complete conversion of anhydrous form I to the desired monohydrate within 24 hours.

The conditions to obtain the X-Ray powder diffraction (XRD) of Example 3 are essentially the same as the conditions described in Example 2.

Thus, a prepared sample of the title compound is characterized by an XRD pattern using CuKa radiation as having diffraction peaks (2-theta values) as described in Table 3 below. Specifically the pattern contains a peak at 13.57 in combination with one or more of the peaks selected from the group consisting of 6.75, 9.71, 16.35, 16.98 and 19.54 with a tolerance for the diffraction angles of 0.2 degrees.

TABLE 3

X-ray powder diffraction peaks of Example 3

| Peak | Angle (2-Theta °) | Intensity (%) |
|---|---|---|
| 1 | 6.75 | 14.2 |
| 2 | 9.71 | 18.3 |
| 3 | 11.35 | 12.5 |
| 4 | 13.57 | 100.0 |
| 5 | 16.35 | 15.6 |
| 6 | 16.98 | 48.8 |
| 7 | 19.54 | 11.5 |
| 8 | 20.40 | 13.0 |

EXAMPLE 4

8-[5-(1-Hydroxy-1-methylethyl)pyridin-3-yl]-1-[(2S)-2-methoxypropyl]-3-methyl-1,3-dihydro-2H-imidazo[4,5-c]quinolin-2-one malate

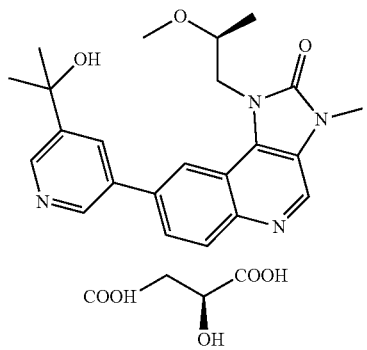

Example 4 can be prepared by suspending free base (53.5 mg) in acetone (2 mL) and then incorporating L-malic acid (22 mg). Solids dissolve into a clear solution. The white crystalline solids precipitate from the solution. Vacuum filter and air dry the solids. Dry the malate salt in vacuum oven (65° C.) overnight to provide the title compound.

The conditions to obtain the X-Ray powder diffraction (XRD) of Example 4 are essentially the same as the conditions described in Example 2.

Thus, a prepared sample of the title compound is characterized by an XRD pattern using CuKa radiation as having diffraction peaks (2-theta values) as described in Table 4 below. Specifically the pattern contains a peak at 5.39 in combination with one or more of the peaks selected from the group consisting of 10.33, 12.16, 15.57 and 20.08 with a tolerance for the diffraction angles of 0.2 degrees.

TABLE 4

X-ray powder diffraction peaks of Example 4

| Peak | Angle (2-Theta °) | Intensity (%) |
|---|---|---|
| 1 | 5.39 | 100.00 |
| 2 | 10.33 | 38.8 |
| 3 | 11.81 | 12.1 |

TABLE 4-continued

X-ray powder diffraction peaks of Example 4

| Peak | Angle (2-Theta °) | Intensity (%) |
|---|---|---|
| 4 | 12.16 | 40.4 |
| 5 | 13.20 | 17.5 |
| 6 | 15.57 | 30.7 |
| 7 | 16.22 | 16.3 |
| 8 | 16.47 | 20.7 |
| 9 | 19.26 | 26.6 |
| 10 | 20.08 | 55.9 |
| 11 | 20.46 | 42.9 |
| 12 | 21.86 | 26.3 |
| 13 | 22.51 | 24.7 |
| 14 | 24.08 | 46.5 |
| 15 | 24.68 | 12.3 |
| 16 | 25.59 | 35.0 |
| 17 | 28.11 | 26.4 |

TABLE 5

X-ray powder diffraction peaks of Example 5

| Peak | Angle (2-Theta °) | Intensity (%) |
|---|---|---|
| 1 | 5.10 | 100.00 |
| 2 | 8.55 | 17.1 |
| 3 | 12.14 | 6.0 |
| 4 | 15.45 | 26.7 |
| 5 | 15.78 | 11.0 |
| 6 | 18.50 | 5.9 |
| 7 | 19.94 | 7.4 |
| 8 | 20.88 | 5.1 |
| 9 | 21.55 | 4.5 |
| 10 | 22.50 | 14.5 |
| 11 | 24.92 | 7.9 |
| 12 | 26.41 | 5.9 |

EXAMPLE 5

8-[5-(1-Hydroxy-1-methylethyl)pyridin-3-yl]-1-[(2S)-2-methoxypropyl]-3-methyl-1,3-dihydro-2H-imidazo[4,5-c]quinolin-2-one fumarate

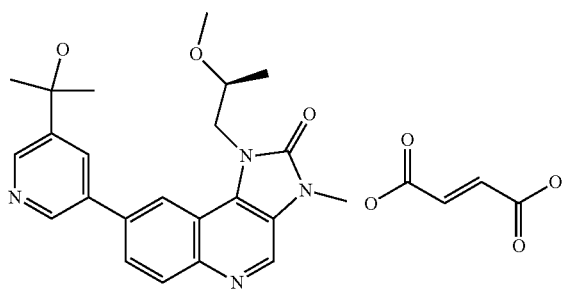

Example 5 can be prepared as by adding free base 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one (60.2 mg) to 1-butanol (0.5 mL) and then add 21.9 mg fumaric acid. Add heptane (5×0.5 mL), which produces thick white slurry, and stir at 90° C./500 rpm. Vacuum filter and dry under nitrogen. Solids are lost during recovery from filtration, though sufficient for XRD. Additional crystalline fumarate salt is prepared by adding free base (101.0 mg) to 1-butanol (0.5 mL) and then add 34 mg fumaric acid. Add heptane (6×0.5 mL) and crystalline seeds of the fumarate salt from first preparation and stir the mixture at 90° C./500 rpm for 1 hour. Recover the solids by vacuum filtration and dry the solids under nitrogen. Further dry the solids in a vacuum oven (65° C.) overnight to provide the title compound.

The conditions to obtain the X-Ray powder diffraction (XRD) of Example 5 are essentially the same as the conditions described in Example 2.

Thus, a prepared sample of the title compound is characterized by an XRD pattern using CuKa radiation as having diffraction peaks (2-theta values) as described in Table 5 below. Specifically the pattern contains a peak at 5.10 in combination with one or more of the peaks selected from the group consisting of 8.55, 15.45, 15.78 and 22.50 with a tolerance for the diffraction angles of 0.2 degrees.

mTOR (FRAP1) In Vitro Enzyme Assay

Use the mTOR LanthaScreen™ Kinase Assay (Invitrogen) to determine compound $IC_{50}$ values against mTOR kinase. This is a Time Resolved Fluorescence Resonance Energy Transfer (TR-FRET) assay format that uses long-lifetime terbium labeled antibody as the donor species and Green Fluorescent Protein (GFP) labeled 4E-BP1 as the acceptor species. Use the TR-FRET ratio to monitor mTOR activity where an increase in phosphorylation of the protein results in an increase in the TR-FRET ratio. Perform the kinase reaction using a 12.5 microliter reaction volume in shallow black 384-well Proxiplate. Add reagents to obtain final reaction conditions of 50 millimolar N-2-hydroxyethylpiperazine-N'-2-ethanesulfonic acid (HEPES) pH 7.5, 1 millimolar ethylene glycol-bis(β-amino ethylether)-N,N,N',N'-tetraacetic acid (EGTA), 0.01% Tween 20, 10 mM manganese chloride, 2 mM DL-dithiothreitol (DTT), 0.4 micromolar GFP-4E-BP1 (a physiological substrate of mTOR, 4E-BP1 expressed and purified as a fusion with green fluorescent protein, Invitrogen), 70 ng per milliliter mTOR (recombinant human mTOR, residues 1360-2549, glutathione-S-transferase (GST)-tagged, expressed in insect cells, Invitrogen), 4% dimethyl sulfoxide and serial dilutions of compound (diluted 1:3 from 20,000 to 1 nM). Add enzyme and substrate to compound and then add adenosine triphosphate (ATP) to 10 μM to start the reaction. Incubate at room temperature for 60 min and then add 12.5 μL of antibody dilution buffer containing 4 nM terbium labeled anti-phospho-threonine-46 4E-BP1 antibody and 20 mM ethylenediaminetetraacetic acid (EDTA), 0.67 mM tris(hydroxymethyl)aminoethane hydrochloride (Trizma®) pH 7.5, 0.02% sodium azide and 0.01% nonylphenylpolyethylene glycol (Nonidet® P40). Incubate at RT for 60 min, and read in an EnVision plate reader with 340 nm wavelength excitation filter and emission filters of 495 nm and 520 nm wavelengths. Use the signal measured with 520 nm filter (specific to GFP) over the signal measured with 495 filter (specific to terbium) to calculate the TR-FRET ratio. Derive the $IC_{50}$ value for each compound using percent inhibition data which is calculated from the reaction data relative to on-plate controls (TR-FRET ratio of assay data points relative to no ATP on-plate controls). Use ACTIVITYBASE 4.0 to fit the percent inhibition and ten-point compound concentration data to a four-parameter logistic equation.

A compound within the scope of the invention is tested in this assay run substantially as above. For example, the compound of Example 1 is tested and found to have an absolute IC50 value of 0.165 μM (±0.0925, n=5). These results indicate that compounds within the scope of the present invention are potent inhibitors of mTOR.

Phosphoinositide 3-Kinase Alpha (PI3Ka) In Vitro Enzyme Assay

Use the PI3Ka Scintillation Proximity Assay (PI3Ka SPA) to determine compound $IC_{50}$ values against PI3Ka kinase. This assay assesses the activity PI3Ka in the presence of compound inhibitors by measuring incorporation of $\gamma$-$P^{33}$-ATP into phosphatidylinositol (4,5) bisphosphate ($PIP_2$). Perform the kinase reactions in 40 µL reaction volumes in 96-well half-area flat bottom white with clear bottom polystyrene plates. Add PI3Ka to start the reaction. Final reaction conditions are 43.75 mM 2,2-bis(hydroxymethyl)-2,2',2"-nitrilotriethanol (Bis-Tris) pH 7.0, 306 mM sodium chloride (NaCl), 1.76 mM polyethylene glycol octylphenyl ether (Triton™ X-100), 10 µM adenosine triphosphate (ATP), 2.9 mM magnesium chloride ($MgCl_2$) and 1 µCi per well $\gamma$-$P^{33}$-adenosine triphosphate ($\gamma$-$P^{33}$-ATP), 5.0 nM PI3Ka human recombinant enzyme, 0.2 mM palmitoyl-oleoyl phosphatidylserine (POPS), 0.04 mM phosphatidylinositol (4,5) bisphosphate ($PIP_2$), 4% DMSO and serial dilutions of compound (diluted 1:3 from 20,000 to 1 nM). Incubate at RT for 90 min after adding PI3Ka. Stop the reaction with the addition of 40 µL of a stopping buffer containing 2.5 mg/mL neomycin linked beads (Amersham, Cat# RPNQ0506) and 21 mM ethylenediaminetetraacetic acid (EDTA). Centrifuge plates for 30 min at 1000 revolutions per minute (RPM) and count radioactivity with a Wallac Microbeta Trilux normalized for $P^{33}$. Derive the $IC_{50}$ value for Example 1 by using percent inhibition data calculated using the reaction data relative to on-plate controls (active enzyme versus 62.5 millimolar EDTA-inhibited enzyme controls). Fit the percent inhibition and ten-point compound concentration data to a four-parameter logistic equation using ACTIVITYBASE 4.0.

A compound within the scope of the invention is tested in this assay run substantially as above. For example, the compound of Example 1 is tested and found to have an absolute IC50 value of 0.00607 µM (±0.00338, n=2). These results show that compounds within the scope of the present invention are potent inhibitors of PI3Ka.

Phosphoinositide 3-Kinase Beta (PI3Kb) In Vitro Enzyme Assay

Use the PI3K beta Scintillation Proximity Assay (PI3K beta SPA) to determine the IC50 value against PI3Kb for a compound. This assay assesses the activity PI3K beta in the presence of compound inhibitors by measuring incorporation of $\gamma$-P33-ATP into phosphatidylinositol (4,5) bisphosphate (PIP2). Perform the kinase reactions in 40 µL reaction volumes in 96-well half-area flat bottom white with clear bottom polystyrene plates. Add PI3K beta to start the reaction. Final reaction conditions are 43.75 mM 2,2-bis(hydroxymethyl)-2,2',2"-nitrilotriethanol (Bis-Tris) pH 7.0, 87.5 mM sodium chloride (NaCl), 1.76 mM polyethylene glycol octylphenyl ether (Triton™ X-100), 40 µM adenosine triphosphate (ATP), 1.0 mM magnesium chloride (MgCl2) and 1 µCi per well $\gamma$-P33-adenosine triphosphate ($\gamma$-P33-ATP), 6.0 nM PI3K beta human recombinant enzyme, 0.2 mM palmitoyl-oleoyl phosphatidylserine (POPS), 0.04 mM phosphatidylinositol (4,5) bisphosphate (PIP2), 4% DMSO and serial dilutions of compound (diluted 1:3 from 20,000 to 1 nM). Incubate at RT for 90 min after adding PI3K beta. Stop the reaction with the addition of 40 µL of a stopping buffer containing 2.5 mg/mL neomycin linked beads (Amersham, Cat# RPNQ0506) and 21 mM ethylenediaminetetraacetic acid (EDTA). Centrifuge plates for 30 min at 1000 revolutions per minute (RPM) and count radioactivity with a Wallac Microbeta Trilux normalized for P33. Derive the IC50 value for the compound by using percent inhibition data calculated using the reaction data relative to on-plate controls (active enzyme versus 62.5 millimolar EDTA-inhibited enzyme controls). Fit the percent inhibition and ten-point compound concentration data to a four-parameter logistic equation using ACTIVITYBASE 4.0.

A compound within the scope of the invention is tested in this assay run substantially as above. For example, the compound of Example 1 is tested and found to have an absolute IC50 value of 0.0776 µM (±0.0401, n=2). These results show that compounds within the scope of the present invention are potent inhibitors of PI3Kb.

Phosphoinositide 3-Kinase Delta (PI3Kd) and Phosphoinositide 3-Kinase Gamma (PI3Kg) In Vitro Enzyme Assays Use the Adapta® kinase assay for the fluorescent based immunoassay detection of ADP. This is a Time Resolved-FRET (TR-FRET) assay format that uses a Europium labeled anti-ADP antibody and an Alexa Fluor® 647 (AF647) labeled ADP tracer to monitor kinase ADP production. Use the TR-FRET ratio to monitor PI3K delta or PI3K gamma activity where an increase in lipid phosphorylation and the corresponding increased ADP production results in a decrease in the TR-FRET.

Enzyme Reactions: Perform the kinase reaction for PI3Kd using a 10 microliter reaction volume in a Corning®, low volume, white 384 well plate (Corning® #3674). Add reagents to obtain final reaction conditions of 0.47-2.6 nanograms PI3K delta (recombinant full length human PI3Kd expressed in and purified from insect cells, Invitrogen) and 50 micromolar PIP2: PS in 32.5 millimolar HEPES, pH 7.5, 50 millimolar sodium chloride, 0.015% CHAPS, 1.5 millimolar magnesium chloride, 0.5 millimolar EGTA, 25 micromolar ATP, 1% DMSO and serial diluted compound (diluted 1:3 from 20,000 to 1 nanomolar). Add the ATP to compound and then add the substrate/kinase mixture to start the reaction. Shake the plate for 30 seconds and then incubate at room temperature for 60 minutes. Perform the kinase reaction for PI3Kg using a 10 microliter reaction volume in a Corning®, low volume, white 384 well plate (Corning® #3674). Add reagents to obtain final reaction conditions of 3.5-26 nanograms PI3K gamma (recombinant full length human PI3Kg expressed in and purified from insect cells, Invitrogen) and 50 micromolar PIP2: PS in 32.5 millimolar HEPES, pH 7.5, 0.5 millimolar EGTA, 1.5 millimolar magnesium chloride, 25 micromolar ATP, 1% DMSO and serial diluted compound (diluted 1:3 from 20,000 to 1 nanomolar). Add the ATP to compound and then add the substrate/kinase mixture to start the reaction. Shake the plate for 30 seconds, centrifuge 2 minutes at 1000×g and then incubate at room temperature for 60 minutes.

ADP Detection: Add 5 microliter of Detection Mix (30 mM EDTA, 30 nM Eu-anti ADP antibody and the EC60 concentration of ADP tracer for reactions with 5-100 µM ATP, Invitrogen) to PI3K delta and gamma enzyme reactions. Shake the plate for 30 seconds, centrifuge 2 minutes at 1000×g and then incubate at room temperature for 60 minutes. Read the plates on a fluorescent plate reader using 340 nm wavelength excitation filter and emission filters of 665 nm and 615 nm wavelengths. Use the signal measured with 665 nm filter (specific to AF647 poly GT emission) over the signal measured with 615 filter (specific to europium) to calculate the TR-FRET ratio. Use the TR-FRET ratio to calculate ADP concentration by calculation back to an ATP/ADP standard curve which is fit to a sigmoidal dose-response model number 205 (XLfit from IDBS). Derive IC50 value for each compound using the percent inhibition data which is calculated from the reaction data relative to on-plate controls (ADP concentration of assay data points relative to no ATP on-plate controls). Use XLfit (IDBS) to fit the percent inhibition and ten-point compound concentration data to a sigmoidal dose-response model 205 (XLfit from IDBS).

A compound within the scope of the invention is tested in these assays run substantially as above. For example, the compound of Example 1 is tested and found to have an absolute IC50 value of 0.0380 μM for PI3Kd and an absolute IC50 value of 0.0238 μM for PI3Kg. These results show that compounds within the scope of the present invention are potent inhibitors of PI3Kd and PI3Kg.

DNA-Dependent Protein Kinase (DNA-PK) In Vitro Enzyme Assay

Use the Z'LYTE® kinase assay format (Invitrogen) to determine IC50 values against DNA-PK for a compound. This is a fluorescence based, coupled enzyme assay format based on sensitivity of phosphorylated vs. nonphosphorylated dual labeled peptide substrate (Coumerin on amino terminus, Fluorescein on carboxy terminus) to proteolysis. Use the Fluorescence Resonance Energy Transfer (FRET) ratio to monitor DNA-PK activity where phosphorylation of the peptide protects the peptide from proteolytic cleavage and the FRET of the substrate is maintained. Perform the kinase reaction using 10 microliter reaction volume in a Corning®, low volume NBS, black 384 well plate (Corning® #3676). Add reagents to obtain final reaction conditions of 50 millimolar N-2-hydroxyethylpiperazine-N'-2-ethanesulfonic acid (HEPES) pH 7.5, 0.01% BRIJ-35 nonionic surfactant, 10 millimolar magnesium chloride, 1 millimolar ethylene glycol-bis (β-amino ethylether)-N,N,N',N'-tetraacetic acid (EGTA), 1 mM DL-dithiothreitol (DTT), 2.5 microgram/milliliter Calf Thymus-DNA (CT DNA), 3.88-27.3 nanogram DNA-PK, 2 micromolar of the Ser/Thr 26 labeled peptide (Invitrogen), 1% dimethyl sulfoxide and serial dilutions of compound (diluted 1:3 from 20,000 to 1 nanomolar). Add enzyme and substrate to compound then add 25.0 micromolar adenosine triphosphate (ATP) to start the reaction. Shake the plate for 30 seconds then incubate at room temperature for 60 minutes. Add 5 microliter of a 1:16 dilution of Development Reagent Solution B (Invitrogen), shake the plate for 30 seconds and then incubate at room temperature for 60 minutes. Read the plate on a fluorescence plate reader with 400 nm wavelength excitation filter and emission filters of 445 and 520 nm. Use the signal measured with 445 nm filter (specific to Coumarin) over the signal measured with 520 filter (specific to fluorescein) to calculate the FRET ratio. Derive the IC50 value for the compound using percent inhibition data calculated from the reaction data relative to on-plate controls (DMSO control for 0% inhibition and no ATP reaction for 100% inhibition). Use XLfit (IDBS) to fit the percent inhibition and ten-point compound concentration data to a sigmoidal dose-response model (model number 205).

A compound within the scope of the invention is tested in this assay run substantially as above. For example, the compound of Example 1 is tested and found to have an absolute IC50 value of 0.00424 μM. These results show that compounds within the scope of the present invention are potent inhibitors of DNA-PK.

AlphaScreen SureFire Detection of Phosphorylated p70S6 Kinase (Thr389), AKT (Thr308), and AKT (Ser473) in U87MG Cells Use the AlphaScreen SureFire® for p-p70S6 kinase (Thr389) (TGR Biosciences, TGRAS50K), p-AKT(Thr308) (TGR Biosciences, TGRA2S50K), and p-AKT(Ser473) (TGR Biosciences, TGRAS50K) to determine the effect of Example 1 on the formation of endogenous phosphorylated p70S6 kinase (Thr389), AKT(Thr308) and AKT(Ser473) respectively. This homogeneous assay format uses immunosandwich capture of the phosphorylated analyte and then detection with antibody-coated Alphascreen beads to generate an amplified signal.

Maintain U87MG cells in U87MG growth medium consisting of DMEM (GIBCO 11965-092) supplemented with 10% fetal bovine serum (FBS, GIBCO, 10091-141), 1% nonessential amino acids (GIBCO, 11140-050) and 1% sodium pyruvate (GIBCO, 11360-070). Harvest cells using standard cell culture procedures and then count using Vi-Cell. Plate 100 μL of U87MG cells in growth medium (50,000 cells/well) into Costar #3596 96 well plates and incubate overnight at 37° C., 5% $CO_2$.

On the day of the assay, treat cells with Example 1 (20 μL/well) diluted in media containing 6% DMSO. Incubate for one h at 37° C., then remove the medium and add 50 μL of 1× SureFire Lysis Buffer (TGR Biosciences SureFire® Kit component) to each well and incubate at room temperature for 10 min with gentle shaking. Transfer 6 μL lysate and 10 μL reaction mixture (60 parts reaction buffer/10 parts activation buffer/1 part each of donor and acceptor beads, Perkin Elmer, 6760617R) to a 384 well proxiplate (Perkin Elmer, 6006280) for the p-p70S6 kinase (Thr389) and p-AKT(Ser473) assays. Seal the plate and incubate at RT for 4 h. Transfer 4 μL lysate and 5 μL reaction mixture (40 parts reaction buffer/10 parts activation buffer/1 part acceptor bead) to a 384 well proxiplate for the p-AKT (Thr308) assay. Incubate 2 h at RT and then add 2 μL dilution mixture (20 parts dilution buffer/1 part donor bead) to each well. Seal the plate and incubate at RT for another 2 h. Read the plates on a Perkin Elmer EnVision equipped with a TurboModule using standard AlphaScreen® settings ($Ex_{680nm}$ and $Em_{520-620nm}$). Calculate percent inhibition data from the reaction data relative to on-plate control. Then use ACTIVITYBASE 4.0 to fit the percent inhibition from the ten-point compound concentration data to a four-parameter logistic equation to derive the $IC_{50}$ value for Example 1.

A compound within the scope of the invention is tested in this assay run substantially as above. For example, the compound of Example 1 is tested and found to have absolute IC50 values as provided in Table 6. These results show that compounds within the scope of the present invention inhibit enzymes in PI3K and mTOR pathway in U87MG cells.

TABLE 6

| Example | AKT1 (pT308) Absolute $IC_{50}$ (μM) | AKT1 (pS473) Absolute $IC_{50}$ (μM) | P70S6 (pT389) Absolute $IC_{50}$ (μM) | S6RP (pS240/242) Absolute $IC_{50}$ (μM) |
|---|---|---|---|---|
| 1 | 0.106 (±0.0649, n = 4) | 0.0942 (±0.0421, n = 4) | 0.0106 (±0.00296, n = 4) | 0.0191 (±0.00204, n = 3) |

Cell Proliferation Assay

Use the CellTiter-Glo Luminescent Cell Viability Assay System (commercially available from Promega) to measure the antiproliferation activity of Example 1 by determining the number of viable cells in culture based on quantitation of the ATP present, which signals the presence of metabolically active cells.

Plate cells in a 96-well plate at 2000 cells/well in 100 µL of cell specific medium (for U87MG use DMEM, 10% FBS, 25 mM 4-(2-hydroxyethyl)-1-piperazineethanesulfonic acid (HEPES), 1.0 mM sodium pyruvate, and 0.1 mM Non Essential Amino Acids (ATCC Cat.#30-2002); for HT1080 use Eagle's MEM, 10% FBS (ATCC Cat.#30-2003); for H1975, A2780, SJSA-1 and 786-O use RPMI 1640, 10% FBS (ATCC Cat.#30-2001); for A204 use McCoy's 5A, 10% FBS (ATCC Cat.#30-2007) except in column 1 use medium only as the blank control. Incubate the plates overnight at 37° C. and 5% $CO_2$. On the next day, prepare compound stocks at 1 mM in DMSO and serially dilute in DMSO in a 96-well round bottom polypropylene plate. Assay compounds at 10 concentrations in duplicate, 4 compounds per plate.

Transfer 4 µL of the DMSO serial dilutions to a 96 well plate and add 196 µL of culture medium to create a 10× stock for dosing. Gently transfer 11 µL of each dosing stock to the corresponding well of the cell plate resulting in a 0.2% DMSO concentration and a 111 µL final volume. Add 11 µL medium to the control columns (Column 12) and background columns (Column 1). Incubate cells with compound for at 37° C., 5% $CO_2$ for 72 or 96 h (For H1975, 786-O, HT1080, A2780, A204 and SJSA-1 use 72 h and for U87MG use 96 h).

Prepared the CellTiter-Glo reagent (Promega, Cat: G7571) and add 100 L to each well after the incubation is complete, homogenize the cells by mixing on an orbital shaker for 2 min and then incubate at RT for 10 min to allow the luminescent signal to stabilize. Record the luminescent raw data with a Wallac Victor V plate reader. Calculate the IC50 values for Example 1 using percent inhibition data. A four-parameter logistic curve is fit to each dose response.

A compound within the scope of the invention is tested in this assay run substantially as above. For example, the compound of Example 1 is tested and found to have absolute IC50 values as provided in Table 7. These results indicate that compounds within the scope of the present invention are useful in inhibiting the proliferation of U87MG, H1975, 786-O, A2780, HT-1080, A204, and SJSA-1 cell lines.

TABLE 7

| U87MG $IC_{50}$ (µM) | H1975 $IC_{50}$ (µM) | 786-O $IC_{50}$ (µM) | A2780 $IC_{50}$ (µM) | HT-1080 $IC_{50}$ (µM) | A204 $IC_{50}$ (µM) | SJSA-1 $IC_{50}$ (µM) |
| --- | --- | --- | --- | --- | --- | --- |
| 0.074 | 0.102 | 0.126 | 0.090 | 0.072 | 0.097 | 0.096 |

Oncotest Tumor Clonogenic Assay

Use the Oncotest (GmbH of Freiburg, Germany) collection of human tumor xenografts grown subcutaneously in immune deficient nude mice to measure the response to Example 1 to a variety of tumor types. The xenografts, directly transplanted from patients to and passaged in nude mice, retain most of the characteristics of the parental patient tumors including histology and sensitivity to anticancer drugs that recapitulate the response of the donor patient to standard anticancer drugs to a high extent. Prepare tumor cells directly from human tumor xenografts growing in nude mice. Measure the inhibition of anchorage independent colony formation of the tumor cells in soft agar.

Test Example 1 in the patient derived human tumor xenograft models shown in Table 10, which comprise 2 to 10 models of 13 different human tumor histotypes, namely bladder cancer, colon, gastric, head and neck, non small cell lung (adeno, squamous cell and large cell), mammary, ovary, pancreatic, prostate, and renal cancer, as well as melanoma, pleuramesothelioma, and sarcoma, where and is moderately differentiated, pd is poorly differentiated, ud is undifferentiated, and wd is well differentiated.

Preparation of Single Cell Suspensions from Human Tumor Xenografts

Grow solid human tumor xenografts subcutaneously in serial passages in thymus aplastic nude mice (NMRI nu/nu strain) and remove tumors under sterile conditions, mechanically disaggregate and subsequently incubate with an enzyme cocktail consisting of collagenase type IV (41 U/ml), DNase I (125 U/ml), hyaluronidase (100 U/ml) and dispase II (1.0 U/ml) in RPMI 1640-Medium at 37° C. for 45 minutes. Pass the cells through sieves of 200 µm and 50 µm mesh size and wash twice with sterile PBS-buffer. Determine the percentage of viable cells in a Neubauer-hemocytometer using trypan blue exclusion.

Clonogenic Assay Procedure with Cells from Human Tumor Xenografts

Perform the clonogenic assay in a 24-well format according to a modified two-layer soft agar assay (Hamburger et al., Science 197:461-643, 1997). The bottom layer consists of 0.2 ml/well IMDM (supplemented with 20% (v/v) fetal calf serum, 0.01% (w/v) gentamicin) and 0.75% (w/v) agar. Add $0.8 \cdot 10^4$ to $5 \cdot 10^4$ cells to 0.2 mL of the same culture medium supplemented with 0.4% (w/v) agar and plate onto the bottom layer in 24-well dishes. Apply the test compound by continuous exposure (drug overlay) in 0.2 mL culture medium. Add the drug overlay 24 hours after seeding the cells as 3-fold concentrated solution. Include six untreated control wells and 6 concentrations of drug-treated groups in triplicate in every dish. Incubate cultures at 37° C. and 7.5% $CO_2$ in a humidified atmosphere for up to 20 days and monitor closely for colony growth using an inverted microscope. Within this period, in vitro tumor growth leads to the formation of colonies with a diameter of >50 µm. At the time of maximum colony formation, count colonies with an automatic image analysis system (OMNICON 3600, Biosys GmbH). Stain vital colonies 24 hours prior to evaluation with a sterile aqueous solution of 2-(4-iodophenyl)-3-(4-nitrophenyl)-5-phenyltetrazolium chloride (1 mg/ml, 100 µl/well).

Express the drug effects in terms of the percentage of colony formation. Compare the mean number of colonies in the treated wells with the mean colony count of the untreated controls (express the relative colony count by the test-versus-control-group value, T/C-value [%]):

$$\frac{T}{C}[\%] = \frac{\text{colony count}_{treated\ group}}{\text{colony count}_{control\ group}} \cdot 100$$

Plot compound concentration versus relative colony count and determine the absolute IC50 and IC70 values, or the drug concentrations necessary to inhibit colony formation by 50% (T/C=50%) and 70% (T/C=30%), respectively by a two-point-curve-fit.

A compound within the scope of the invention is tested in this assay run substantially as above. For example, the compound of Example 1 is tested and found to have absolute IC50 values as provided in Table 8. These results indicate that compounds within the scope of the present invention are useful in inhibiting the proliferation of these patient derived cell lines.

TABLE 8

Human xenografts examined in the clonogenic assay

| Tumor designation | Tumor model | Histology | Absolute IC50 (mM) |
|---|---|---|---|
| Bladder | BXF 1218 | transitional cell carcinoma | 0.048 |
|  | BXF 1228 | transitional cell carcinoma, wd | 0.031 |
| Colon | CXF 1103 | adeno carcinoma, pd | >0.2 |
|  | CXF 1729 | adeno carcinoma, wd | 0.176 |
|  | CXF 1783 | colon carcinoma, wd | 0.029 |
|  | CXF 243 | adeno carcinoma, pd | 0.237 |
|  | CXF 280 | adeno carcinoma, pd | 0.007 |
|  | CXF 676 | adeno carcinoma, md | 0.35 |
|  | CXF 975 | adeno carcinoma, md | 0.142 |
| Gastric | GXF 1172 | signet-ring cell carcinoma, pd | 0.141 |
|  | GXF 209 | signet-ring cell carcinoma, ud | 0.184 |
|  | GXF 97 | adeno carcinoma, wd | 0.101 |
| Head and Neck | HNXF 536 | squamous epithelium carcinoma, wd | 0.055 |
|  | HNXF 908 | squamous epithelium carcinoma, md | 0.052 |
| NSCLC | LXFA 1041 | adeno carcinoma, md | 0.205 |
|  | LXFA 1584 | adeno carcinoma, pd | 0.085 |
|  | LXFA 526 | adeno carcinoma, pd | 0.084 |
|  | LXFA 629 | adeno carcinoma, pd | 0.026 |
|  | LXFA 983 | adeno carcinoma, pd | 0.103 |
|  | LXFE 1422 | squamous cell carcinoma, ud | 0.231 |
|  | LXFE 211 | squamous cell carcinoma, ud | 0.108 |
|  | LXFL 1072 | large cell lung carcinoma, pd | 0.214 |
|  | LXFL 430 | large cell lung carcinoma, pd | 0.056 |
|  | LXFL 529 | large cell lung carcinoma, pd | 0.128 |
| Mammary | MAXF 1322 | pap. adeno carcinoma, pd | 0.003 |
|  | MAXF 1384 | adeno carcinoma, pd | 0.243 |
|  | MAXF 401 | pap. adeno carcinoma, wd | 0.15 |
|  | MAXF 583 | ductual adeno carcinoma, md | 0.088 |
| Melanoma | MEXF 1539 | amelanotic melanoma, md | 0.246 |
|  | MEXF 276 | amelanotic melanoma, md | 0.157 |
|  | MEXF 462 | amelanotic melanoma, md | 0.156 |
|  | MEXF 989 | amelanotic melanoma, md | 0.185 |
| Ovary | OVXF 1353 | adeno carcinoma, pd | >.2 |
|  | OVXF 550 | carcinoma | 0.028 |
|  | OVXF 899 | pap. serous adeno carcinoma, md | 0.59 |
| Pancreas | PAXF 546 | inf., mucous squamous cell carcinoma | 0.105 |
|  | PAXF 736 | adeno carcinoma, pd | 0.174 |
| Prostate | PRXF DU145 | adeno carcinoma, ud | 0.269 |
|  | PRXF PC3M | adeno carcinoma, metastatic, pd | 0.208 |
| Pleuramesothelioma | PXF 1752 | pleuramesothelioma | 0.032 |
|  | PXF 541 | invasive pleuramesothelioma | 0.056 |
| Renal | RXF 1220 | hypernephroma, pd | 0.191 |
|  | RXF 393 | hypernephroid carcinoma, pd | 0.044 |
|  | RXF 486 | hypernephroid adeno carcinoma, clear cell | 0.112 |
|  | RXF 631 | hypernephroid adeno carcinoma, wd | 0.08 |
| Sarcoma | SXF 1186 | osteoblastic osteosarcoma, md | 0.11 |
|  | SXF 1301 | malignant rhabdomyosarcoma, ud | >0.2 |
|  | SXF 627 | pleomorphic rhabdomyosarcoma, pd | 0.095 |

E545 Kp110a Leukemia Model

Leukemia cell line creation: Transduce embryonic liver cells derived from transgenic embryos, B6.Cg-Tg[IghMyc]22Bri/J (Jackson Laboratory, Bar Harbor, Me.), with a retrovirus expressing a clinically-isolated activating mutation of human p110α (E545K as an amino acid change, G1633A on the nucleotide level) under control of the viral 5' LTR (long terminal repeat) and expressing GFP (green fluorescent protein) under control of the PGK promoter (MSCV6 FLAG-p110α G1633A PGK/GFP) to create target-driven leukemia cells. Transfer the transduced cells into a lethally irradiated host animal. The transduced cells repopulate the hematopoietic stem cells among bone marrow of the recipient and rescue the recipient animal from radiation-induced lethality due to ablation of the recipient's original bone marrow. Observe the rescued primary animals for development of leukemia via weekly monitoring white blood cell counts in a small amount of blood (10 μL) collected retro-orbitally. Collect blood from primary irradiated animals with confirmed leukemia and serially passage to secondary (non-irradiated) host animals in order to establish as a leukemic cell line.

Subject Animals: Use female C57BL/6 mice (Taconic, Cambridge City, Ind.), 8 to 10 week old and 20 to 22 g in weight, as leukemia recipient animals. Acclimate animals on normal low fat diet (4.5%) prior to inoculation and continue on that diet ad libitum for the duration of the study. Identify individual mice from each group by ear punches. Inoculate animals with leukemic cells from donor animals (day 0).

Syngeneic leukemia model: From a donor animal previously inoculated with the leukemic cell line of interest, collect a small amount of blood retro-orbitally (10 µL) and measure the leukemia cell burden by white blood cell count. From animals with sufficient leukemic burden, collect donor blood, dilute with phosphate-buffered saline (PBS) to 500,000 white blood cells per 200 µL and inject 200 µL per animal retro-orbitally on day 0 to initiate leukemia. Assign mice inoculated with p110α(E545K)/myc cells to groups of five for treatment with Example 1 and a group of ten for a vehicle treated control group. On day 5 through day 11 post-inoculation, dose each group daily by oral gavage with vehicle only; Example 1 at 5, 10, 20 mg test article QD per kilogram body weight (mg/kg). Collect at least 10 µL blood retro-orbitally from animals on day 12 to assess leukemia progression in the leukemia cell assay.

Leukemia Cell Assay: Collect ten (10) µL of whole blood from each study animal and process on a Coulter TQ-Prep such that red blood cells are lysed and fix the remaining nucleated leukocytes for analysis. Analyze the fixed cells immediately or store them in the dark at 4° C. for future analysis. Assay the cells by Fluorescent Antibody Cell Sorting (FACS) analysis with a Cytomics FC 500 (Beckman Coulter). Count leukemic cells within a specific region of the forward-scatter/side-scatter (FS/SS) plot in each sample (defined as a region showing little/no leukemic cells in normal animals yet significant leukemic cells in leukemic control animals). Normalize these data as leukemic cells per unit volume of blood by use of a fixed cutoff of Beckman Coulter Flow-Count Fluorospheres per sample (uniform amount of Fluorospheres originally added to each initial blood sample where equal counts per sample would equate to equal volume counted per sample).

Test Article: On a weekly basis, mix Example 1 with 1% Hydroxyethylcellulose (HEC)/0.25% Polysorbate 80/0.05% Antifoam/Purified Water and sonicate with a probe sonicator to suspend. Refrigerate the formulated test article at 4° C. and store in the dark until used (re-suspend prior to each administration).

Statistical Analyses: Tabulate the Flow cytometry data with the Beckman Coulter's CXP software. Determine the statistical significance of the effects of Example 1 with Dunnett's method, one-way ANOVA using the vehicle group as the control group (JMP Statistical Discovery Software, SAS Institute).

A compound within the scope of the invention is tested in this assay run substantially as above. For example, the compound of Example 1 is tested and found to have % TGI values as provided in Table 9. These results indicate that compounds within the scope of the present invention inhibit the growth of a tumor whose growth is driven by mutant E545K PI3Ka, one of the hotspot mutations found in many human cancers.

TABLE 9

E545Kp110a leukemia model results for Example 1

| Dose (mg/kg) | Schedule | % TGI | % TGI SEM |
|---|---|---|---|
| 5 | qd | 50.5 | 7.7 |
| 10 | qd | 76.1 | 5.0 |
| 20 | qd | 90.1 | 4.1 |

% TGI is % tumor growth inhibition vs control untreated group
% TGI SEM is % TGI standard error of the mean Xenograft Tumor Models Expand human glioblastoma cells U87MG and human renal carcinoma cells 786-O, in culture, harvest and inject subcutaneously onto the rear flank of athymic nude mice. Expand human non-small cell lung cancer cells NCI-H1975 in culture, harvest and inject subcutaneously onto the rear flank of CD-1 nu/nu mice. Prepare test compound in an appropriate vehicle and administer by oral gavage when tumors are established (7-21 days after implant). Tumor response is determined by tumor volume measurement performed twice a week during the course of treatment. Body weight is taken as a general measurement of toxicity.

A compound within the scope of the invention is tested in this assay run substantially as above. For example, the compound of Example 1 is tested and found to have % TGI values as provided in Table 10. These results indicate that compounds within the scope of the present invention are useful in demonstrating dose dependent anti-tumor activity in the U87MG, 786-O, and NCI-H1975 models.

TABLE 10

| Tumor Model | Dose (mg/kg) | Schedule | % TGI | % TGI SE |
|---|---|---|---|---|
| U87MG | 3 | BID | 38.6 | 13 |
| U87MG | 6 | BID | 57.7 | 6.6 |
| U87MG | 10 | BID | 86.1 | 1.3 |
| U87MG | 12 | QD | 53.4 | 10.1 |
| 786-O | 3 | BID | 33.9 | 7.8 |
| 786-O | 6 | BID | 56.9 | 6.7 |
| 786-O | 10 | BID | 70.2 | 4 |
| H1975 | 3 | BID | 13.8 | 10.4 |
| H1975 | 6 | BID | 26.9 | 9.6 |
| H1975 | 10 | BID | 62.7 | 7.4 |

% TGI is % tumor growth inhibition vs. control untreated group, % TGI SEM is % TGI standard error of the mean, and the underlined values indicate significance.

Determination of PI3Ka and mTOR In Vivo Target Inhibition

Implant U87MG human glioblastoma cells ($5 \times 10^6$) subcutaneously into the flank of athymic nude mice in 0.2 mL of matrigel. Ten days post-implantation, dose mice orally according to a time course, single dose/single time point, or dose response protocol for the determination of $TMED_{50}$ (threshold minimum effective dose). Flash freeze tumors at harvest and collect blood for the determination of parent compound plasma exposure and the calculation of $TMEC_{50}$ (threshold minimum effective concentration) in the case of dose response studies. Homogenize tumors in 500 µL of XY Lysis Buffer (10 µg/mL Leupeptin, 10 µg/mL Trypsin-Chymotrypsin Inhibitor, 10 µg/mL Tosyl phenyl-alanyl chloromethyl ketone, 10 µg/mL Aprotinin, 60 mM Beta-Glycerol Phosphate, 1% Triton X100, 25 mM Tris pH 7.5, 2.5 mM Pyrophosphate, 150 mM NaCl, 2 mM p-tosyl-L-arginine methyl ester, 15 mM para-nitrophenyl phosphate, 5 mM benzamidine, 1 mM sodium vanadate, 10 mM sodium fluoride, 50 µg/mL phenyl-methane sulfonyl fluoride, 1 mM 1,4-dithiothreitol (DTT), 15 mM EDTA pH 8.0, 5 mM EGTA pH 8.0, 1 µM Microcystin, 1 µM Okadaic Acid, and 1 Roche Complete protease inhibitor mini-tablet per 10 mL) using RNase Free Pellet Pestle (Kimble-Kontes). Aliquot lysates and either assay immediately or store at −80° C. for later testing. Use the multiplex format of Meso Scale Discovery (Gaithersburg, Md.) ELISA technology and measure in vivo target inhibition of PI3K and mTOR to assess effects on phosphorylation of the threonine 308 site of AKT, a downstream effector of PI3K; phosphorylation on the threonine 389 site of p70 S6K and on the serine 240/244 site of S6RP, downstream effectors of mTORC1; phosphorylation of the serine 473 site of AKT, a downstream effector of mTORC2. Add 20 μg of lysate to carbon electrode containing 96-well plates pre-spotted with the appropriate capture antibodies. Probe the protein of interest using a ruthenium labeled detection antibody. Pass current over the electrode in the presence of read buffer containing the co-reactant TPA, and quantitate and record the light generated by electro-chemiluminescence with the MSD Sector 6000 instrument. Calculate percent inhibitions relative to the vehicle control group and perform ANOVA analysis using the JMP software package for the determination of statistical significance.

A compound within the scope of the invention is tested in this assay run substantially as above. For example, the compound of Example 1 is tested and found to have the activity as provided in Table 11, where the underlined values indicate significance. These results indicate that compounds within the scope of the present invention demonstrate the ability to inhibit PI3K and mTOR in vivo.

TABLE 11

| Dose (mg/kg) | Post Dose (hr) | pT308 AKT % inhibition | pS473 AKT % inhibition | pT389 p70S6K % inhibition | pS240/244 S6RP % inhibition |
|---|---|---|---|---|---|
| 3 | 0.25 | 28 | 23 | 77 | −11 |
| 3 | 0.5 | <u>43</u> | <u>63</u> | <u>89</u> | 9 |
| 3 | 1 | 7 | 12 | <u>89</u> | <u>51</u> |
| 3 | 3 | 7 | −7 | <u>77</u> | <u>64</u> |
| 3 | 4 | −2 | −3 | <u>64</u> | <u>37</u> |
| 6 | 0.25 | <u>47</u> | <u>63</u> | <u>88</u> | 7 |
| 6 | 0.5 | <u>61</u> | <u>77</u> | <u>91</u> | 26 |
| 6 | 1 | <u>41</u> | <u>67</u> | <u>90</u> | <u>66</u> |
| 6 | 2 | 32 | <u>51</u> | <u>87</u> | <u>83</u> |
| 6 | 4 | 1 | −5 | <u>68</u> | <u>58</u> |
| 6 | 6 | −4 | −8 | <u>61</u> | <u>55</u> |
| 6 | 12 | −16 | −6 | 14 | <u>−35</u> |
| 10 | 0.5 | <u>88</u> | <u>90</u> | <u>93</u> | −4 |
| 10 | 1 | <u>71</u> | <u>73</u> | <u>92</u> | <u>69</u> |
| 10 | 2 | <u>53</u> | <u>66</u> | <u>92</u> | <u>89</u> |
| 10 | 4 | <u>44</u> | <u>56</u> | <u>91</u> | <u>95</u> |
| 10 | 8 | 13 | 13 | <u>55</u> | 16 |
| 0.5 | 0.5 | 23 | −9 | <u>62</u> | 9 |
| 1.5 | 0.5 | 28 | <u>34</u> | <u>84</u> | 4 |
| 3 | 0.5 | <u>43</u> | <u>63</u> | <u>89</u> | 9 |
| 6 | 0.5 | <u>61</u> | <u>77</u> | <u>91</u> | 26 |
| 12 | 0.5 | <u>79</u> | <u>91</u> | <u>92</u> | <u>55</u> |
| 0.5 | 4 | 1 | −28 | 7 | 5 |
| 1.5 | 4 | −8 | −12 | <u>38</u> | 12 |
| 3 | 4 | −2 | −3 | <u>64</u> | 37 |
| 6 | 4 | 1 | −5 | <u>68</u> | <u>58</u> |
| 12 | 4 | <u>43</u> | 44 | <u>90</u> | <u>97</u> |

Solubility Determination

Prepare a 2 mg/mL solution of Example 2 in each of the required media by weighing approximately 1 mg of compound into a vial and add the required volume (i.e. 0.5 mL) of the corresponding media into each vial. Place capped vial on a rotating mixture over night (~16 hours) at ambient conditions, then filter using 0.22 um Ultrafree-MC filters (Millipore™) and measure pH of filtrate (Orion 720A pH meter). Prepare the sample for HPLC analysis by transferring 100 μL of the filtrate into a HPLC vial and add 900 μL of 50% acetonitrile/water solution. Determine solubility using HPLC method (HPLC mobile phase of 15% Acetonitrile with 0.1% TFA and 85% Water with 0.1% TFA; column Bonus RP, 4.6×75 mm, 3.5 cm; Detector at 264 nm UV; Column Temperature=40° C.; Flow Rate 1.5 mL/min; Injection Volume=1 μL).

TABLE 12

Solubility Results

| | Example 2 | |
|---|---|---|
| Sample Media | Average mg/mL | Average pH |
| 0.1N HCl | ≧2.0 | 1.15 |
| pH 2* | ≧2.0 | 2.31 |
| pH 4* | 1.0524 | 4.92 |
| pH 6* | 0.7178 | 6.14 |
| pH 8* | 0.6352 | 8.00 |
| SGF* | 1.7529 | 3.52 |
| Fed* | ≧2.0 | 5.09 |
| Fast* | 1.0203 | 6.45 |

*pH 2 = 50 mM phosphate buffer at pH 2
pH 4 = 50 mM phosphate buffer at pH 4
pH 6 = 50 mM phosphate buffer at pH 6
pH 8 = 50 mM phosphate buffer at pH 8
SGF = Simulated gastric fluid (Aburub et al., Int. J. of Pharmaceutics, 347: 16-22, 2008).
Fed = Simulated intestinal fluid fed state (Dressman J et al., Pharma. Res., 15(1): 11-21, 1998).
Fast = Simulated intestinal fluid fasted state (Dressman J et al., Pharma. Res., 15(1): 11-21, 1998)

A compound within the scope of the invention is tested in this assay run substantially as above. For example, the compound of Example 2 is tested and found to have the solubility results as provided in Table 12. These results indicate that Example 2 demonstrates desirable solubility over the physiological pH of the gastro intestinal tract (GIT). This physicochemical property will help avoid variability in exposure in oncology patients who will most likely be on multiple medications such as proton pump inhibitors (PPI) which may result in drug-drug interactions with drug that have variable solubility over the physiological pH of the GIT. This is because changes in the pH of the stomach (i.e. patients taking or not taking PPI's or food effects) may result in exposure variability due to solubility differences. The avoidance of potential drug-drug interactions is especially important in oncology, because of the numerous drugs cancer patients usually receive at the same time, the narrow therapeutic window of many anti-cancer drugs and the greater inter- and intra individual variability in patients. A compound having desirable solubility also avoids the need for complex and expensive formulations that may be used to increase systemic exposure required for efficacy due to low solubility or reduce exposure variability due to food effects and PPI.

Pharmacokinetic Properties in Dogs

Beagle dogs are routinely used to determine in vivo exposure and pharmacokinetic parameters of pharmaceutical products. While canine gastrointestinal physiology differs in some aspects from that of humans, it is useful for predicting drug absorption and identifying potential problems with non-linear pharmacokinetics To determine pharmacokinetic parameters of Example 1 in dogs, male and female dogs (up to 4 animals per dose, in separate studies) are given Example 1 via oral gavage in a 1% hydroxyethylcellulose, 0.25% polysorbate 80, 0.05% antifoam in purified water suspension ("HEC suspension"). The range of administered doses is between 1 and 12 mg/kg in an HEC suspension.

Blood samples are collected into tubes containing potassium ethylenediaminetetraacetic acid from each dog at 0 (predose), 0.5, 1, 2, 4, 8, and 24 hours post dose. Some studies also include samples collected at 0.25 hr and 12 hr time points. These samples are centrifuged to obtain plasma, which is subsequently frozen prior to analysis. The samples undergo protein precipitation and the extracts are analyzed for the presence of Example 1 by liquid chromatography/tandem mass spectrometry, using a PE-Sciex API4000 mass spectrometer. The standard curves range from 1 to 5000 ng/mL. Plasma concentrations above the upper limit of quantitation are determined by dilution. Measured concentrations of Example 1 are stored in Watson v.7.4, a validated Laboratory Information Management System utilized for storing and managing electronic data, and pharmacokinetic parameters are calculated by noncompartmental analysis using the WATSON software.

A compound within the scope of the invention is tested in this assay run substantially as above. For example, the compound of Example 1 is tested and found to have the mean AUC as provided in Table 13. The area under the curve (AUC) values of Example 1 increase linearly with dose in the range of 1 to 12 mg/kg as shown in the table below. Linear regression analysis of individual AUC values results in a correlation of determination $R^2$ of 0.86 and a linear equation of y=1474.3x+44.311. Linear regression analysis of the mean AUC values for each dose results in a correlation of determination $R^2$ 0.96 and a linear equation of y=1544.7x−735.34. These results indicate that compounds within the scope of the present invention have linear pharmacokinetic properties in dogs over a pharmacologically relevant dose range, with no evidence of saturation of absorption. This is a favorable property for drug development and clinical administration, allowing predictable increases in systemic exposure with oral administration.

TABLE 13

| | Dose (mg/kg) | | | | | |
|---|---|---|---|---|---|---|
| | 1 | 3 | 4.5 | 6 | 9 | 12 |
| Mean AUC ± Standard Deviation (ng*hr/mL) | 1161 ± 440 | 3783 ± 2163 | 5920 ± 269 | 9620 ± 2093 | 10790 ± 5954 | 19150 ± 3465 |

TABLE 13-continued

| | Dose (mg/kg) | | | | | |
|---|---|---|---|---|---|---|
| | 1 | 3 | 4.5 | 6 | 9 | 12 |
| Number of animals | 10 | 10 | 2 | 2 | 2 | 2 |

We claim:

1. A compound which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one, or a pharmaceutically acceptable salt thereof.

2. The compound according to claim 1 which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one.

3. The compound according to claim 2 which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one in crystalline form characterized by a X-ray powder diffraction pattern having characteristic peaks, in 2θ±0.2, occurring at 8.57 and one or more of 9.06, 15.93, 18.29, and 18.87.

4. A pharmaceutical composition comprising a compound which is 8-[5-(1-hydroxy-1-methylethyl)pyridin-3-yl]1-[(2S)-2-methoxypropyl]-3-methyl-1,3-dihydro-2H-imidazo[4,5-c]quinolin-2-one, or a pharmaceutically acceptable salt thereof, and a pharmaceutically acceptable carrier, diluent, or excipient.

5. The pharmaceutical composition according to claim 4 comprising the compound which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one.

6. The pharmaceutical composition according to claim 5 comprising the compound which is 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one in crystalline form characterized by a X-ray powder diffraction pattern having characteristic peaks, in 2θ±0.2, occurring at 8.57 and one or more of 9.06, 15.93, 18.29, and 18.87.

* * * * *